(12) United States Patent
Harris et al.

(10) Patent No.: US 8,394,402 B2
(45) Date of Patent: Mar. 12, 2013

(54) COMPOSITIONS AND METHODS FOR THE SUSTAINED RELEASE OF BETA-ALANINE

(71) Applicant: Natural Alternatives International, Inc., San Marcos, CA (US)

(72) Inventors: Roger Harris, New Market (GB); John Wise, San Marcos, CA (US)

(73) Assignee: Natural Alternatives International, Inc., San Marcos, CA (US)

( * ) Notice: Subject to any disclaimer, the term of this patent is extended or adjusted under 35 U.S.C. 154(b) by 0 days.

(21) Appl. No.: 13/646,184

(22) Filed: Oct. 5, 2012

(65) Prior Publication Data

US 2013/0030052 A1    Jan. 31, 2013

Related U.S. Application Data

(62) Division of application No. 12/064,005, filed as application No. PCT/US2006/020104 on May 23, 2006, now Pat. No. 8,329,207.

(60) Provisional application No. 60/683,985, filed on May 23, 2005.

(51) Int. Cl.
*A61K 47/00* (2006.01)
*A61K 31/195* (2006.01)

(52) U.S. Cl. ...................... 424/439; 514/561

(58) Field of Classification Search .............. None
See application file for complete search history.

(56) References Cited

U.S. PATENT DOCUMENTS

| | | |
|---|---|---|
| 3,934,036 A | 1/1976 | Irikura |
| 3,966,988 A | 6/1976 | Wilson et al. |
| 4,120,852 A | 10/1978 | Bauer et al. |
| RE30,370 E | 8/1980 | Pittet et al. |
| 4,328,245 A | 5/1982 | Yu et al. |
| 4,409,239 A | 10/1983 | Yu |
| 4,410,545 A | 10/1983 | Yu et al. |
| 4,522,811 A | 6/1985 | Eppstein et al. |
| 4,713,244 A | 12/1987 | Bawa et al. |
| 4,761,399 A | 8/1988 | Pilotto et al. |
| 4,883,861 A | 11/1989 | Grill et al. |
| 5,190,775 A | 3/1993 | Klose |
| 5,561,110 A | 10/1996 | Michaelis et al. |
| 5,612,375 A | 3/1997 | Sueoka |
| 5,767,159 A | 6/1998 | Hultman et al. |
| 5,866,537 A | 2/1999 | Bianchi |
| 5,869,068 A | 2/1999 | De Lacharriere et al. |
| 5,965,596 A | 10/1999 | Harris et al. |
| 5,976,559 A | 11/1999 | De Lacharriere et al. |
| 6,013,286 A | 1/2000 | Klose |
| 6,019,999 A | 2/2000 | Miller et al. |
| 6,071,888 A | 6/2000 | Rihova et al. |
| 6,172,098 B1 | 1/2001 | Harris et al. |
| 6,426,361 B2 | 7/2002 | Harris et al. |
| 6,517,868 B2 | 2/2003 | Fassihi |
| 6,585,999 B1 | 7/2003 | King et al. |
| 6,680,294 B2 | 1/2004 | Harris et al. |
| 6,696,500 B2 | 2/2004 | Hata et al. |
| 6,756,049 B2 | 6/2004 | Brubaker et al. |
| 6,835,397 B2 | 12/2004 | Lee et al. |
| 6,919,372 B1 | 7/2005 | Yamashita et al. |
| 6,992,065 B2 | 1/2006 | Okumu |
| 7,048,947 B2 | 5/2006 | Kamei et al. |
| 7,504,376 B2 | 3/2009 | Harris et al. |
| 7,825,084 B2 | 11/2010 | Harris et al. |
| 8,067,381 B1 | 11/2011 | Harris et al. |
| 8,129,422 B2 | 3/2012 | Harris et al. |
| 2004/0229773 A1 | 11/2004 | Harris et al. |
| 2009/0005293 A1 | 1/2009 | Harris et al. |
| 2009/0220575 A1 | 9/2009 | Harris et al. |
| 2011/0009346 A1 | 1/2011 | Harris et al. |
| 2012/0190717 A1 | 7/2012 | Harris et al. |

FOREIGN PATENT DOCUMENTS

| | | |
|---|---|---|
| DE | 3424781 A1 | 1/1985 |
| EP | 0280593 | 8/1988 |
| EP | 0 449787 A2 | 10/1991 |
| EP | 1210940 A2 | 6/2002 |
| JP | 54-159393 A | 12/1979 |
| JP | 61-204120 | 9/1986 |
| JP | 64-042425 | 2/1989 |
| JP | 03095125 A | 4/1991 |
| JP | 04095026 A | 3/1992 |
| JP | 04112825 A | 4/1992 |
| JP | 06024976 A | 2/1994 |
| JP | 07-236460 | 9/1995 |
| JP | 7-236460 A | 9/1995 |
| JP | 07-509230 | 10/1995 |
| JP | 7509230 T | 10/1995 |
| JP | 08-224073 | 9/1996 |
| JP | 2002-51730 | 2/2002 |
| WO | WO-90/06102 A1 | 6/1990 |
| WO | WO-93/04690 A1 | 3/1993 |
| WO | WO-98/06278 A1 | 2/1998 |
| WO | WO 2004/091497 | 10/2004 |
| WO | WO-2007/073398 A3 | 9/2007 |

OTHER PUBLICATIONS

Dunnett et al., "Carnosine, anserine and taurine contents in individual fibres from the middle gluteal muscle of the camel," Res. Vet. Sci., 62:213-216 (1997).*

Dunnett et al., "Determination of carnosine and other biogenic imidazoles in equine plasma by isocratic reversed-phase ion-pair high-performance liquid chromatography," J. Chromatogr. 579:45-53 (1992).*

(Continued)

*Primary Examiner* — Robert A Wax
*Assistant Examiner* — Jessica Worsham
(74) *Attorney, Agent, or Firm* — Patton Boggs LLP

(57) ABSTRACT

Methods and compositions are provided for increasing the anaerobic working capacity of muscle and other tissues. Also provided are compositions formulated for the sustained release of free beta-alanine. Also provided is a dietary supplement formulated, for example, as a solid food product, an edible suspension, liquid or semi-liquid as described herein.

10 Claims, 2 Drawing Sheets

OTHER PUBLICATIONS

Dunnett et al., "Plasma carnosine concentration: diurnal variation and effects of age, exercise and muscle damage," Equine Vet. J. Suppl. 34:283-287 (2002).*

Dunnett, "High performance liquid-chromatographic determination of N-alpha-acetyl-L-carnosine in equine plasma," J. Chromatogr. B. Biomed. Sci. Appl. 688:150-154 (1997).*

Stout et al., "Effects of β-alanine supplementation on the onset of neuromuscular fatigue and ventilatory threshold in women," Amino Acids 32:381-386 (2007).*

Office Action in Inter Partes Reexamination, for Patent No. 8,067,381 (Application No. 95/002,001), mail date Jul. 26, 2012 from the United States Patent and Trademark Office, 19 pages.

Office Action in Inter Partes Reexamination, for Patent No. 8,129,422 (Application No. 95/002,048), mail date Aug. 17, 2012 from the United States Patent and Trademark Office, 24 pages.

Office Action in Inter Partes Reexamination, for Patent No. 8,129,422 (Application No. 95/002,048), mail date Oct. 16, 2012 from the United States Patent and Trademark Office, 28 pages.

Order Granting Request for Inter Partes Reexamination, for Patent No. 8,067,381, mail date Jul. 26, 2012 from the United States Patent and Trademark Office in U.S. Application No. 95/002,001, 19 pages.

Order Granting Request for Inter Partes Reexamination, for Patent No. 8,129,422, mail date Aug. 17, 2012 from the United States Patent and Trademark Office in U.S. Application No. 95/002,048, 22 pages.

In the U.S. Patent and Trademark Office, First Preliminary Amendment in re: U.S. Appl. No. 13/215,073, dated Aug. 22, 2011, 6 pages.

In the U.S. Patent and Trademark Office, Information Disclosure Statement in re: U.S. Appl. No. 13/215,073, dated Aug. 22, 2011, 12 pages.

In the U.S. Patent and Trademark Office, Report on the filing or determination of an action regarding a patent in re: U.S. Appl. No. 12/806,356, dated Jun. 19, 2012, 11 pages.

In the U.S. Patent and Trademark Office, Notice of Allowance in re: U.S. Appl. No. 12/806,356, dated Oct. 21, 2011, 7 pages.

In the U.S. Patent and Trademark Office, Notice of Allowance in re: U.S. Appl. No. 12/806,356, dated Jul. 11, 2011, 1 page.

In the U.S. Patent and Trademark Office, Office Action in re: U.S. Appl. No. 12/806,356, dated May 12, 2011, 5 pages.

In the U.S. Patent and Trademark Office, Reexam Office Action in re: Reexam Application No. 95/002,001, dated Jul. 26, 2012, 19 pages.

In the U.S. Patent and Trademark Office, Determination—Reexam Ordered in re: Reexam Application No. 95/002,001, dated Jul. 26, 2012, 19 pages.

In the U.S. Patent and Trademark Office, Reexam Office Action in re: Reexam Application No. 95/002,048, dated Oct. 16, 2012, 28 pages.

In the U.S. Patent and Trademark Office, Determination—Reexam Ordered in re: Reexam Application No. 95/002,048, dated Aug. 17, 2012, 22 pages.

In the U.S. Patent and Trademark Office, Reexam Office Action in re: Reexam Application No. 95/002,048, dated Aug. 17, 2012, 24 pages.

In the U.S. Patent and Trademark Office, Notice of Allowance in re: U.S. Appl. No. 12/064,005, dated Oct. 30, 2012, 9 pages.

In the U.S. Patent and Trademark Office, Notice of Allowance in re: U.S. Appl. No. 12/064,005, dated Oct. 2, 2012, 12 pages.

In the U.S. Patent and Trademark Office, Office Action in re: U.S. Appl. No. 12/064,005, dated May 7, 2012, 17 pages.

In the U.S. Patent and Trademark Office, Final Office Action in re: U.S. Appl. No. 12/064,005, dated Oct. 6, 2011, 16 pages.

In the U.S. Patent and Trademark Office, Office Action in re: U.S. Appl. No. 12/064,005, dated Apr. 5, 2011, 18 pages.

In the U.S. Patent and Trademark Office, Requirement for Restriction/Election in re: U.S. Appl. No. 12/064,005, dated Jan. 26, 2011, 8 pages.

In the U.S. Patent and Trademark Office, Notice of Allowance in re: U.S. Appl. No. 12/231,240, dated May 25, 2010, 4 pages.

In the U.S. Patent and Trademark Office, Office Action in re: U.S. Appl. No. 12/231,240, dated Oct. 19, 2010, 5 pages.

In the U.S. Patent and Trademark Office, Notice of Allowance in re: U.S. Appl. No. 09/318,530, dated Jul. 20, 2000, 2 pages.

In the U.S. Patent and Trademark Office, Notice of Allowance in re: U.S. Appl. No. 13/215,073, dated Oct. 17, 2011, 7 pages.

In the U.S. Patent and Trademark Office, Office Action in re: U.S. Appl. No. 13/356,182, dated Aug. 3, 2012, 5 pages.

In the U.S. Patent and Trademark Office, Notice of Allowance in re: U.S. Appl. No. 10/717,217, dated Oct. 30, 2008, 5 pages.

In the U.S. Patent and Trademark Office, Notice of Allowance in re: U.S. Appl. No. 10/717,217, dated Oct. 2, 2008, 6 pages.

In the U.S. Patent and Trademark Office, Notice of Allowance in re: U.S. Appl. No. 10/717,217, dated May 30, 2008. 7 pages.

In the U.S. Patent and Trademark Office, Notice of Allowance in re: U.S. Appl. No. 10/717,217, dated Apr. 25, 2008, 4 pages.

In the U.S. Patent and Trademark Office, Office Action in re: U.S. Appl. No. 10/717,217, dated Sep. 21, 2007, 9 pages.

In the U.S. Patent and Trademark Office, Requirement for Restriction/Election in re: U.S. Appl. No. 10/717,217, dated Jan. 5, 2007, 8 pages.

"Gels for Drug Delivery," *Controlled Release Systems: Fabrication Technology*, 1988, vol. II, Chapter 3, Hsieh (ed.) pp. 41-60.

"Science Lines Up Behind Beta-Alanine—Could it Be the Next Creatine?" Retrieved from the Internet:<URL: subscribers.nutritionbusinessjournal.com/supplements/science_lines_up_beta_0906/wall.html?return=http://subscribers.nutritionbusinessjournal.com/supplements/science_lines_up_beta_0906/index.html, Sep 1, 2006 [retrieved on Apr. 14, 2010] [2 pages].

Admin, Beta-Alanine Review, (May 23, 2008) Retrieved from: www.musclesweb.net/blog/beta-alanine-review/ [Retrieved on Jan. 5, 2010] [2 pages].

Ansel, *Introduction to Pharmaceutical Dosage Forms*, 4th Ed., 1985, p. 126.

Asatoor et al., "Intestinal absorption of carnosine and its constituent amino acids in man," Gut, II:250-254 (1970).

Babizhayev et al., "L-carnosine (beta-alanyl-L-histidine) and carcinine (beta-alanylhistamine) act as natural antioxidants with hydroxyl-radical-scavenging and lipid-peroxidase activities," Biochem J. 304 ( Pt 2):509-516 (1994).

Bakardjiev et al., Transport of Beta-Alanine and biosynthesis of carnosine by skeletal muscle cells in primary culture,: Eur. J. Biochem., 225(2): 617-623 (1994).

Barger et al., "Carnosine, constitution and synthesis," Biochem J 12:402-407 (1918).

Batcombe et al., "Beta-Alanine: science meets real world results," (2006) Retrieved from: www.beta-alanine.net/ [Retrieved on Jan. 5, 2010] [8 pages].

Bauer et al. "Biosynthesis of carnosine and related peptides by skeletal muscle cells in primary culture," Eur. J. Biochem, 219: 43-47 (1994).

Bergström, "Muscle electrolytes in man," Scand. J. Clin. Invest. 14(Suppl. 68):1-110 (1962).

Beta-Alanine. The Facts., Retrieved from: www.betaalanine.info/background-on-beta-alanine/ [Retrieved on Jan. 5, 2010] [2 pages].

Biolo et al., "Insulin action on protein metabolism," Baillière's Clinical Endocrinology and Metabolism, 7(4), (1993).

Brooke et al., "Muscle fiber types: how many and what kind?," Arch. Neruol. 23:369-379 (1970).

Burd et al., "Carnosine in primary afferents of the olfactory system: an autoradiographic and biochemical study," J. Neurosci. 2:244-255 (1982).

Casey et al., "Creatine ingestion favorably affects performance and muscle metabolism during maximal exercise in humans," Am. J. Physiol 271 (Endocrinol. Metab 34): E31-E37 (1996).

Certified English translation of Japanese patent of JP 2002 51730, published Feb. 19, 2002, entitled "Food Product for Sports". [9 pages].

Certified English translation of JP 61-204120, published Sep. 10, 1986 entitled "Immunomodulatory Agent". [7 pages].

Certified English translation of JP 64-042425, published Feb. 14, 1989, entitled "Remedy for Cachexia". [6 pages].

Certified English Translation of Osaka Hospital Pharmacist Association, "Zentei lyakuhin-youran (the directory of pharmacrutical products)," Yakugyojihosya, the fifth impression, 576-577 (1986).

Certified English translation of Skulachev, V., [Carnosine and anserine as specialized pH-buffershydrogen ion carriers—article in Russian] Biokhimiya 57(9):1311-1316 (1992).

Chung, B., Retrieved from the Internet<URL: evidencebasedfitness.blogspot.com/2007/04/beta-alanine-harris-study-this-is-what.html, Apr. 11, 2007 [retrieved on Apr. 14, 2010] [6 pages].

Collegiate Sport Nutrition, CarnoSyn® —Carnosine Synthesizer [Brochure] (4 pages) (2007).

Crim et al., "Creatine Metabolism in Men: Creatine Pool Size and Turnover in Relation to Creatine Intake" J. Nutr. 106 (3):371-381 (1976).

Defendant Vital Pharmaceutical's First Supplemental Response to Plaintiffs Interrogatory No. 12, served Apr. 19, 2011.

Derave et al., "Beta-Alanine supplementation augments muscle carnosine content and attenuates fatigue during repeated isokinetic contraction bouts in trained sprinters," J. Appl. Physiol. 103:17361743 (2007).

Derave et al., "Beta-alanine supplementation augments muscle carnosine content and attenuates fatigue in trained sprinters," National Strength and Conditioning Association Annual Conference, Atlanta, Jul. 2007.

Derave et al., "Creatine supplementation augments skeletal muscle carnosine content in senescence-accelerated mice (SAMP8)," Rejuvenation Res. 11(3):641-647 (2008).

Di Pasquale, "Conditionally essential amino acids," pp. 127-145 in Amino Acids and Proteins for the Athlete, CRC Press:Boca Raton (1997).

Dunnett et al., "Carnosine, anserine and taurine contents in individual fibres from the middle gluteal muscle of the camel," Res. Vet. Sci., 62:213-216 (1997).

Dunnett et al., "Determination of carnosine and other biogenic imidazoles in equine plasma by isocratic reversed-phase ion-pair high-performance liquid chromatography," J. Chromatogr. 579:45-53 (1992).

Dunnett et al., "High-performance liquid chromatographic determination of imidazole dipeptides, histidine, I-methylhistidine and 3-methylhistidine in muscle and individual muscle fibers," J. Chromatogr. B. Biomed. Appl., 688:47-55 (1997).

Dunnett et al., "Influence of oral beta-alanine and L-histidine supplementation on the carnosine content of the gluteus medius," Equine Vet. J. Suppl. 30:499-504 (1999).

Dunnett et al., "Plasma carnosine concentration: diurnal variation and effects of age, exercise and muscle damage," Equine Vet. J. Suppl. 34:283-287 (2002).

Dunnett, "Carnosine metabolism and function in the thoroughbred horse (anaerobic exercise)," Dissertation (Open University) vol. 57/04-C of dissertation abstracts 1143 (1996).

Dunnett, "High performance liquid-chromatographic determination of N-alpha-acetyl-L-carnosine in equine plasma," J. Chromatogr. B. Biomed. Sci. Appl. 688:150-154 (1997).

English language translation of an Examination Report, issued Mar. 29, 2010, in connection with corresponding Chinese Patent Application No. 200680026773.0.

Gardner et al., "Intestinal Absorption of the Intact Peptide Carnosine in Man, and Comparison with Intestinal Permeability to Lactulose," J. of Physiology, 439: 411-422 (1991).

Hama et al., "Intestinal Absorption of β-Alanine, Anserine and Carnosine in Rats," J. Nutr. Sci. Vitaminol, 22: 147-157 (1976).

Harris et al., "Absorption of creatine supplied as a drink, in meat or in solid form," J Sports Science 20:147-151 (2002).

Harris et al., "Beta-alanine Supplementation for 10 weeks significantly increased muscle carnosine levels," IUPS 2005 Meeting Abstract 566.8 from p. A969, Experimental Biology, San Diego, Apr. 2005.

Harris et al., "Carnosine & Taurine contents in individual fibers in human vastus lateralis muscles," J Sports Sci 16: 639-643 (1998).

Harris et al., "Changes in plasma β-alanine concentration following administration of free or peptide bound forms," Experimental Biology Conference, San Diego, Apr. 2003.

Harris et al., "Effect of 14 and 28 days β-alanine (Carnosyn™) supplementation on isometric endurance of the knee extensors," 13th International Conference Biochemistry of Exercise, Seoul, Korea, Oct. 2006.

Harris et al., "Effect of 14 and 28 days β-alanine (Carnosyn™) supplementation on isometric endurance of the knee extensors," 3rd Annual International Society of Sports Nutrition Conference, Las Vegas, Jun. 2006.

Harris et al., "Effect of Combined Beta-alanine and creatine monohydrate supplementation on exercise performance," Medicine & Science in Sports & Exercise, Journal of the American College of Sports Medicine Conference, San Francisco, 35(5) Supplement 1:s218, May 2003.

Harris et al., "Effects of 14 days of beta-alanine supplementation on isometric endurance of the knee extensors," Medicine and Science in Sports and Exercise 38(5) Supplement, pp. S125-S126, Jun. 2006.

Harris et al., "Elevation of carnosine in muscle of normal subjects by supplementation with b-alanine in free or peptide bound form," Experimental Biology Conference, San Diego, Apr. 2003.

Harris et al., "Muscle buffering capacity and dipeptide content in the thoroughbread horse, greyhound dog and man," Comp. Biochem. Physiol. 97A(2):249-251 (1990).

Harris et al., "The absorption of orally supplied beta-alanine and its effect on muscle carnosine synthesis in human vastus lateralis," Amino Acids 30:279-289 (2006).

Harris et al., "The carnosine content of V lateralis in vegetarians and omnivores," FASEB Journal 21(6):A944, Experimental Biology, Washington D.C., Apr. 2007.

Harris et al., "The distribution of carnosine and taurine in different muscle fibre types from human v lateralis and the effects of beta-alanine supplementation," 9th International Congress on Amino Acids & Proteins, Vienna, Aug. 2005.

Harris et al., "The distribution of carnosine in different muscle fibre types with beta-alanine supplementation," IUPS 2005 Meeting Abstract 665.36 from p. A1125, Experimental Biology, San Diego, Apr. 2005.

Harris et al., "The effect of 4 to 10w dietary supplementation with beta-alanine (free or peptide bound form) on the carnosine content of muscle, and types I and II muscle fibres," J Sport Sci: Annual Conference of the British Association of Sport and Exercise Sciences Loughborough, Sep. 4-7, 2005, 23(11):1171-1172 (2005).

Harris et al., "The effect of a β-alanine supplement on the muscle carnosine content during training," Experimental Biology, San Francisco, Abstract 483.35, Apr. 2006.

Harris et al., "The effect of a β-alanine supplement on the muscle carnosine content during training," Experimental Biology, San Francisco, Apr. 2006.

Harris et al., "The effect of combined beta-alanine and creatine monohydrate supplementation on exercise performance," J. Am. College of Sports Medicine, 35 Supplement 1 :s218, 2003.

Harris et al., "The effect of very high interval training on the carnosine content and buffering capacity of V lateralis from humans," Experimental Biology, Washington D.C., Apr. 2007.

Harris et al., "The effect of whole body physical training on the carnosine content of V lateralis," Experimental Biology, Washington D.C., Apr. 2007.

Harris et al., "The influence of B-alanine supplementation and training on the muscle carnosine content in human v lateralis, and the effect of this on exercise performance," 9th International Congress on Amino Acids & Proteins, Vienna, pp. 12-13, Aug. 2005.

Harris et al., "The plasma concentration-time profile of beta-alanine using a controlled-release formulation (Carnosyn®)," Meeting Abstract, The FASEB Journal 22:701.9 (2008).

Hill et al., "Influence of b-alanine supplementation on skeletal muscle carnosine concentrations and high intensity cycling capacity," Amino Acids 32:225-233 (2007).

Hill et al., "The effect of combined Beta-Alanine and Creatine Monohydrate Supplementation on Muscle Composition and Exercise Performance," Medicine & Science in Sports and Exercise 37(5) Supplement, S348, Jun. 2005.

Hoffman et al., "Beta-alanine and the hormonal response to exercise," Int. J. Sports Med. 29:952-958 (2008).

Hoffman et al., "Effect of Creatine and β-Alanine Supplementation on Performance and Endocrine Responses in Strength/Power Athletes," Int J Sport Nutr Exerc Metab. 16(4):430-446 (2006).

Hoffman et al., "Short-duration β-alanine supplementation increases training volume and reduces subjective feelings of fatigue in college football players," Nutrition Research 28:31-3 5 (2008).

Huszti et al., "Effects of 1-histidine administration on the concentrations of histindine in various tissues," Agents Actions 4(3):183 (1974).

Jones et al., "o-Phthaldialdehyde precolumn derivatization and reversed-phase high-performance liquid chromatography of polypeptide hydrolysates and physiological fluids," J. Chromatogr. 266:471-482 (1983).

Jones et al., "The carnosine content of V Lateralis of vegetarians and omnivores," FASEB Journal 21(6):A944, Experimental Biology, Washington D.C., Apr. 2007. Presented at British Association of Sport and Exercise Science, Student Conference, University of Chichester, Apr. 2007.

Kendrick et al., "The effect of 4 weeks beta-alanine supplementation and isokinetic training on carnosine concentrations in type I and II human skeletal muscle fibres." Eur J Appl Physiol . May 2009; 106(1): 131-8. (Epub Feb. 12, 2009).

Kendrick et al., "The effect of β-alanine (Carnosyn™) supplementation on muscle carnosine synthesis during 4 weeks using a one-leg training model," 13th International Conference Biochemistry of Exercise, Seoul, Korea, Oct. 2006.

Kendrick et al., "The effect of β-alanine (Carnosyn™) supplementation on muscle carnosine synthesis during 4 weeks using a one-leg training model," 3rd Annual International Society of Sports Nutrition Conference, Las Vegas, Jun. 2006.

Kendrick et al., "The effect of β-alanine (Carnosyn™) supplementation on muscle carnosine synthesis during a 10 week program of strength training," 3rd Annual International Society of Sports Nutrition Conference, Las Vegas, Jun. 2006.

Kendrick et al., "The effects of 10 weeks of resistance training combined with beta-alanine supplementation on whole body strength, force production, muscular endurance and body composition," Amino Acids 34(4):547-554 (2008). (Epub Jan. 4, 2008).

Li et al., "Bioactivities of Chicken Essence," J. of Food Science, 77: R105-R110 (2012).

Mannion et al., "Carnosine and anserine concentrations in the quadriceps femoris muscle of healthy humans," Eur. J. Appl. Physiol. Occup. Physiol. 64:47-50 (1992).

Marlin et al., "Carnosine content of the middle gluteal muscle in thoroughbred horses with relation to age, sex and training," Comp. Biochem. Physiol. A. 93:629-632 (1989).

Nutzenadel et al., "Uptake and metabolism of beta-alanine and L-carnosine by rat tissues in vitro: role in nutrition," Am J Physiol. 230(3):643-651 (1976).

Order Construing the Terms of U.S. Patent Nos. 5,965,596; 6,172,098; and 6,426,361, dated May 31, 2011.

Reaction rate tends to increase with concentration—phenomenon explained by collision theory, Chemical kinetics, Wikipedia.org. [retreieved from the internet May 23, 2012].

Sale et al., Effect of beta-alanine supplementation on muscle carnosine concentrations and exercise performance, Amino Acids, Epub ahead of print date Dec. 20, 2009. 13 pages.

Sewell et al., "Estimation of the carnosine content of different fibre types in the middle gluteal muscle of the thoroughbred horse," J. Physiol., 455:447-453 (1992).

Smith, "The buffering of muscle in rigor: protein, phosphate and carnosine," J Physiol 92(3):336-343 (1938).

Stout et al., "Effects of 13-alanine supplementation on the onset of neuromuscular fatigue and ventilatory threshold in women," Amino Acids 32:381-386 (2007).

Stout et al., "Effects of 28 days of beta-alanine and creatine monohydrate supplementation on physical working capacity at neuromuscular fatigue threshold," Poster presented at the International Society of Sports Nutrition Annual Conference, New Orleans, (Jun. 16, 2005).

Stout et al., "Effects of twenty-eight days of beta-alanine and creatine monohydrate supplementaion on the physical working capacity at neuromuscular fatigue threshold," J. Strength Cond. Red. 20(4): 928-931 (2006).

Stout et al., "The effect of beta-alanine supplementation on neuromuscular fatigue in elderly (55-92 Years): a double-blind randomized study," Journal of the International Society of Sports Nutrition 5 :21, 6 pages (2008).

Supplemental European Search Report, issued Apr. 21, 2010 in connection with European Patent Application Serial No. 04749952.0.

Supplementary European Search Report and Search Opinion, issued Oct. 7, 2009, in connection with corresponding European Patent Application No. 06848675.2.

Suzuki et al., "High level of skeletal muscle carnosine contributes to the latter half of exercise performance during 30-s maximal cycle ergometer sprinting," Jpn J Physiol 52:199-205 (2002).

Tallon et al., "Acute changes in plasma carnosine, creatine and markers of purine degradation following exercise," Experimental Biology, Washington D.C., Abstract 1b544, Apr. 2007.

Tallon et al., "Carnosine, taurine and enzyme activities of human skeletal muscle fibres from elderly subjects with osteoarthritis and young moderately active subjects," Biogerontology 8:129-137 (2007).

Tallon et al., "Single muscle fibre analysis of carnosine and associated metabolites in Korean breath hold divers (AMA)," Experimental Biology, Washington D.C., Abstract 1b538, Apr. 2007.

Tallon et al., "The carnosine content of vastus lateralis is elevated in resistance-trained bodybuilders," J. Strength Cond. Res. 19:725-729 (2005).

Tallon, "Research Summaries on β-Alanine/Histidine Supplementation and its Role in Hydrogen-Binding, pH-Controlling, and Carnosine Storage in Skeletal Muscle," iSatori Technologies, Product No. 17805, 8 pages (2005). Retrieved from the Internet at URL: http://www.realsolutionsmag.com/pdf/hblk_whtpaper_low.pdf.

Tamaki et al., "Biosynthesis and degradation of carsonine and turnover rate of its constituent amino acid in rats," J. Nurt. Sci. Vitaminol. 26:127-139 (1980).

Wise et al. "Nutritional supplements for sports: aids to exercise performance and recovery," J Amer Nutra Assoc. 3:28-33 (2000).

Wu et al., "Proximate Composition, Free Amino Acids and Peptides Contents in Commercial Chicken and Other Meat Essences," J. of Food and Drug Analysis, 10(3): 170-177 (2002).

Zoeller et al., "Effects of 28 days of beta-alanine and creatine monohydrate supplementation on aerobic power, ventilatory and lactate thresholds, and time to exhaustion," Amino Acids 33:505-510 (2007).

* cited by examiner

COMPOSITIONS AND METHODS FOR THE SUSTAINED RELEASE OF BETA-ALANINE

CROSS-REFERENCE TO RELATED APPLICATIONS

This application is a divisional of U.S. application Ser. No. 12/064,005, filed Apr. 30, 2009, which is a National Stage application under 35 U.S.C. §371, which claims benefit under 35 U.S.C. §119(a) of International Application No. PCT/US2006/020104, filed May 23, 2006, which claims benefit of U.S. Provisional Patent Application No. 60/683,985, filed May 23, 2005, all of which are herein incorporated by reference.

TECHNICAL FIELD

This application relates generally to the fields of pharmaceuticals and physiology and more specifically to compositions and methods for the sustained release of free beta-alanine.

BACKGROUND

Natural food supplements are typically designed to compensate for reduced levels of nutrients in the modern human and animal diet. In particular, useful supplements increase the function of tissues when consumed. It can be particularly important to supplement the diets of humans and particular classes of animals whose normal diet may be deficient in nutrients available only from meat and animal products (e.g. human vegetarians and other animals consuming an herbivorous diet).

In addition, in the sporting and athletic community, natural food supplements which specifically improve athletic ability are increasingly important, such as supplements that promote or enhance physical prowess for leisure or employment purposes. In another example, anaerobic (e.g., lactate producing) stress can cause the onset of fatigue and discomfort that can be experienced with aging. Anaerobic stress can also result from prolonged sub-maximal isometric exercise when the local circulation is partially or totally occluded by the increase in intra-muscular pressure (e.g., during rock climbing) or from exercise involving prolonged breath holding (e.g., free diving, or synchronized swimming) Excessive lactate production can result in the acidification of the intracellular environment.

Previous work demonstrated that carnosine is significantly increased in muscle following administration of beta-alanine or a biological source of beta-alanine (e.g., carnosine) supplementation. The dosing schedule that has been preferred for such administration (i.e., 8 times daily), however, leads to compliance issues and problems with paraesthesia. Thus, there is a need for improved supplements containing free beta-alanine or a biological source thereof in a sustained release formulation to increase compliance and decrease paraesthesia events.

SUMMARY

Administration of a bolus single dose of 2-6 grams of free beta-alanine (or chemically equivalent amounts of compounds which are biological sources of beta-alanine, e.g., carnosine) results in paraesthesia, a significant adverse side-effect with symptoms that include abnormal sensations such as burning, tingling, or a "pins-and-needles" feeling. Sustained release of free beta-alanine directly or from compounds which can act as biological sources of beta-alanine would obviate serious adverse side-effects by attenuating the rise in the blood-plasma concentration of beta-alanine, providing a means to safely and effectively increase carnosine biosynthesis in muscle and to attenuate metabolic acidosis and muscle fatigue during anaerobic activity.

Provided herein are compositions and methods for the sustained release of free beta-alanine or a biological source thereof. In one embodiment, the composition is a pharmaceutical composition containing free beta-alanine or a biological source thereof and an acceptable carrier, where the composition is formulated for the sustained release of free beta-alanine. In another embodiment, the composition is a dietary supplement containing free beta-alanine or a biological source thereof.

Also provided are methods for increasing the anaerobic working capacity of muscle and other tissues. Such methods include providing a composition formulated for the sustained release of free beta-alanine, and administering free beta-alanine or a biological source thereof in an effective amount to increase the synthesis of carnosine in muscle or other tissues.

Pharmaceutical compositions containing free beta-alanine or a biological source thereof and a pharmaceutically acceptable carrier formulated for sustained release of free beta-alanine are provided. In one embodiment, the pharmaceutical composition is a tablet, capsule, or microbeads that can be administered orally. In another embodiment, the pharmaceutical composition is a skin patch or a topical dermatological compound formulated for the sustained release of free beta-alanine. The pharmaceutical composition can be formulated for humans.

Dietary supplements containing free beta-alanine or a biological source thereof are provided. In one embodiment, the dietary supplement is an energy bar, edible suspension or other food product. The dietary supplement can be formulated for humans.

The pharmaceutical composition can include about 0.1-200.0; about 1.0-9.0; about 2.0-8.0; about 3.0-7.0; or about 4.0-6.0 grams (g) of free beta-alanine or the equivalent amount of a biological source thereof. The pharmaceutical composition can be formulated for humans and can include about 0.1-200.0; about 1.0-9.0; about 2.0-8.0; about 3.0-7.0; or about 4.0-6.0 g of free beta-alanine or the equivalent amount of a a biological source thereof.

A dietary supplement can include about 0.1-200.0; about 1.0-9.0; about 2.0-8.0; about 3.0-7.0; or about 4.0-6.0 g of free beta-alanine or the equivalent amount of a biological source thereof. The dietary supplement can be formulated for humans and can include about 0.1-200.0; about 1.0-9.0; about 2.0-8.0; about 3.0-7.0; or about 4.0-6.0 g of free beta-alanine or the equivalent amount of a biological source thereof. In one embodiment, the dietary supplement is an energy bar, edible suspension or food stuff. In one aspect, the dietary supplement contains multiple servings, and containing 0.1-10.0 g of beta-alanine per serving or the equivalent amount of a biological source thereof. The total dosage of free beta-alanine or the equivalent amount of a biological source thereof contained in the dietary supplement can be about 0.1-200.0; about 1.0-8.0; about 3.0-7.0; or about 4.0-6.0 g of free beta-alanine or the equivalent amount of a biological source thereof.

Also provided herein are formulations for the sustained release of free beta-alanine or an equivalent amount of a biological source thereof that are contained in pharmaceutical compositions. In one aspect, a pharmaceutical composition containing free beta-alanine or an equivalent amount of a biological source thereof is formulated for sustained release and can be administered orally in the form of a tablet, gel, or microbeads. In another aspect, the pharmaceutical composition is a topical dermatological formulation such as, for example, a hydrogel formulated for the sustained release of free beta-alanine across the skin.

While not limited by any particular mechanism of action, provided herein are methods and compositions for increasing the anaerobic working capacity of muscle and other tissues. The methods and compositions disclosed herein provide for the accumulation of carnosine within a tissue in the body, resulting from the availability of beta-alanine. The methods include ingesting or infusing compositions containing free beta-alanine or a biological source thereof formulated for sustained release into the body. In one aspect, the compositions are mixtures of compounds capable of increasing the accumulation of beta-alanylhistidine peptides (e.g., carnosine) in human and animal tissue. The compositions can induce the synthesis and accumulation of beta-alanylhistidine peptides in a human or animal body when introduced into the body.

The compositions provided herein can be used for the preparation of a dietary supplement including, e.g., drinks, edible suspensions or foods, or pharmaceutical composition for humans or animals. Compositions of the invention can be used in any of the methods of the invention.

In one aspect, methods are provided for increasing the anaerobic working capacity of a tissue. The method includes the steps of providing free beta-alanine to blood or blood plasma in an amount effective to increase carnosine synthesis in a tissue. The tissue referred to herein can be skeletal muscle.

Therefore, in an exemplary aspect, provided herein are compositions and methods for the sustained release of free beta-alanine comprised in a pharmaceutical composition or in a dietary supplement to increase the anaerobic working capacity of muscle tissue as a result of increased carnosine biosynthesis.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE DRAWINGS

Like reference symbols in the various drawings indicate like elements.

DETAILED DESCRIPTION

Figure 1:
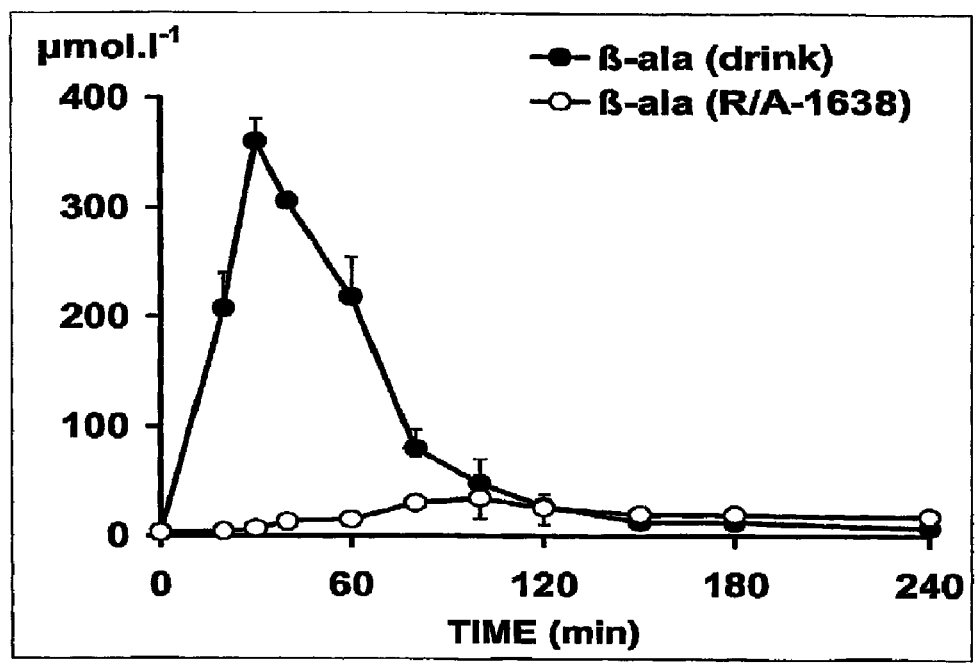
FIG. 1 is a graph showing the blood plasma levels of beta-alanine in individuals after ingesting either a beta-alanine drink or beta-alanine sustained release capsules.

Provided herein are compositions for the sustained release of free beta-alanine. Also provided herein are methods for increasing the anaerobic working capacity of a tissue by providing free beta-alanine to blood or blood plasma in an amount that is effective to increase the synthesis of beta-alanylhistidine peptides, particularly carnosine, in a tissue. Beta-alanylhistidine peptides can include peptides of beta-alanine, such as carnosine, anserine, and balenine. Sustained release of free beta-alanine is desirable to prevent unwanted adverse side effects such as paraesthesia.

Any of the beta-alanine-containing compositions disclosed herein can be formulated as the sole pharmaceutically active ingredient in the composition, or beta-alanine may be combined and/or co-administered with other active ingredients. For example, another active ingredient may be another pharmacological agent known in the general art to be of value to attenuate the metabolic acidosis encountered during high-intensity exercise by increasing carnosine biosynthesis to delay the onset of fatigue during anaerobic exercise. In addition, combinations with creatine are desirable because the ergogenic effect of the formulation is enhanced. Further, the active materials also can be mixed with other active materials which do not impair the desired action, or with materials that supplement the desired action, such as antacids, H2 blockers, and diuretics.

Co-administration as used herein refers to the administration of more than one therapeutic agents in the course of a coordinated treatment to achieve an improved clinical outcome. Such co-administration may also be coextensive; that is, occurring during overlapping periods of time.

A. Beta-Alanine and Muscles

Beta-alanine and L-histidine and their methylated analogues form di-peptides within the human or animal body. The di-peptides produced from beta-alanine and histidine include carnosine (beta-alanyl-L-histidine), anserine (beta-alanyl-L-1-methylhistidine), or balenine (beta-alanyl-L-3-methylhistidine) (referred to generically herein as "beta-alanylhistidine peptides"). Beta-alanylhistidine peptides are involved in the regulation of intra-cellular pH homeostasis during muscle contraction and, therefore, are involved in the development of muscle fatigue. Beta-alanylhistidine peptides provide an effective way of accumulating pH-sensitive histidine residues in a cell. Thus, variations in the muscle beta-alanylhistidine peptide concentrations affect the anaerobic work capacity of muscles, and increasing the amount of beta-alanylhistidine peptides within a muscle favorably affects performance and the amount of work that can be performed by the muscle.

Beta-alanine and L-histidine can be generated within the body or are made available via the diet. Within the body, beta-alanine is transported to tissues such as muscle. Since in a typical fed state, the concentration of beta-alanine in muscle is low in comparison with the concentration of L-histidine, the concentration of beta-alanine is likely limiting to the synthesis of beta-alanylhistidine peptides. The synthesis and accumulation of beta-alanylhistidine peptides in a human or animal body can be increased by increasing the blood or blood plasma concentrations of beta-alanine, increasing the blood or blood plasma concentrations of beta-alanine and creatine, or increasing the blood or blood plasma concentrations of beta-alanine, L-histidine, and creatine (i.e., N-(aminoiminomethyl)-N-glycine, N-amidinosarcosine, N-methyl-N-guanylglycine, or methylglycocyamine).

During sustained intensive exercise or exercise sustained under conditions of local hypoxia, the accumulation of hydronium ions formed during glycolysis and the accumulation of lactate due to anaerobic metabolism can severely reduce the intracellular pH. The reduced pH can compromise the function of the creatine-phosphorylcreatine system. The decline in intracellular pH also can affect other functions within the cells such as the function of the contractile proteins in muscle fibers. Administering beta-alanine to an individual elevated muscle beta-alanylhistidine peptide levels and increased total work capacity of the muscle. In addition, chronic dietary supplementation with beta-alanine can increase muscle beta-alanylhistidine peptide concentration and, thus, increase intramuscular buffering capacity.

Providing beta-alanine or a compound that is a biological source of beta-alanine (e.g., carnosine, anserine, or balanine, and salts and chemical derivatives thereof) is a feasible means by which to attenuate the metabolic acidosis encountered during high-intensity exercise by increasing beta-alanylhistidine peptide biosynthesis and, thus, delay the onset of fatigue during anaerobic exercise. A compound that is a biological source of beta-alanine is defined herein as a compound that, when administered to the body by any route (for example parenterally, orally, topically), is converted by one or more chemical- or enzyme-catalysed reaction steps to beta-alanine, which then appears in blood, plasma or serum and is available for uptake into muscle and other tissues.

The free beta-alanine content of the composition may be present as any active form of beta-alanine or analogues thereof (e.g., esters or salts). The free beta-alanine content of the composition can be subjected to a micronization process (e.g. crushing, pulverizing, powdering and the like) prior to incorporation into the pharmaceutical composition so that the resulting composition is not unacceptably "gritty" in texture.

B. Pharmaceutical Compositions

The compositions provided herein include free beta-alanine or a biological source thereof in combination with a pharmaceutically acceptable carrier that is formulated for sustained release. While one mode of delivery is oral, other modes of delivery of compositions according to this invention can be used. These include mucosal delivery, nasal delivery, ocular delivery, transdermal delivery, parenteral delivery, vaginal delivery, rectal delivery, and intrauterine delivery. The compositions can be in a liquid, semi-liquid or solid form, and can be formulated in a manner suitable for the intended route of administration.

Typically, compositions containing free beta-alanine or a biological source thereof as described herein can be formulated into pharmaceutical compositions using techniques and procedures well known in the art. See, e.g., Ansel, *Introduction to Pharmaceutical Dosage Forms*, 4$^{th}$ Ed., 1985, pg 126. Pharmaceutical carriers or vehicles suitable for administration of free beta-alanine or a biological source thereof include any such carriers known to those skilled in the art that are suitable for the particular mode of administration.

Formulations containing suitable quantities of beta-alanine or a biological source thereof include, for example, capsules, tablets, pills, powders, granules, sterile parenteral solutions or suspensions, oral solutions or suspensions, oil water emulsions as well as implants and microencapsulated delivery systems, and biodegradable, biocompatible polymers such as collagen, ethylene vinyl acetate, polyanhydrides, polyglycolic acid, polyorthoesters, and polylactic acid. Methods for preparing these compositions are known to those skilled in the art.

Formulations for oral delivery can include, for example, tablets, capsules, granules, and bulk powders. Types of oral tablets include compressed, chewable lozenges and tablets which may be enteric coated, sugar coated or film coated. Capsules can be hard or soft gelatin capsules, while granules and powders can be provided in non-effervescent or effervescent form with a combination of other ingredients known to those skilled in the art. By way of example, free beta-alanine or a biological source thereof can be suspended in, for example, propylene carbonate, vegetable oils or triglycerides and encapsulated in a gelatin capsule. Such solutions and the preparation and encapsulation thereof are disclosed, for example, in U.S. Pat. Nos. 4,328,245; 4,409,239; and 4,410,545.

By way of example, enteric coated tablets, because of the enteric coating, resist the action of stomach acid and dissolve or disintegrate in the neutral or alkaline intestines; sugar coated tablets are compressed tablets to which different layers of pharmaceutically acceptable substances are applied; film coated tablets are compressed tablets which have been coated with a polymer or other suitable coating; and multiple compressed tablets are compressed tablets made by more than one compression cycle utilizing the pharmaceutically acceptable substances previously mentioned. Any of these formulations of tablets are suitable for delivering beta-alanine or a biological source thereof.

Free beta-alanine or a biological source thereof may be orally administered in a liquid form. Liquid formulations for oral delivery include aqueous solutions (e.g., elixirs and syrups), emulsions, suspensions, solutions and/or suspensions. Elixirs are clear, sweetened, hydroalcoholic preparations, and pharmaceutically acceptable carriers used in elixirs generally include solvents. Syrups are concentrated aqueous solutions of a sugar, for example, sucrose, and may contain a preservative. An emulsion is a two phase system in which one liquid is dispersed in the form of small globules throughout another liquid. Pharmaceutically acceptable carriers used in emulsions are non aqueous liquids, emulsifying agents and preservatives. Suspensions use pharmaceutically acceptable suspending agents and preservatives.

For the preparation of solutions or suspensions, it is possible to use, for example, water or physiologically acceptable organic solvents such as alcohols (e.g., ethanol, propanol, isopropanol, 1,2-propylene glycol, polyglycols and their derivatives, fatty alcohols, partial esters of glycerol), oils (e.g., peanut oil, olive oil, sesame oil, almond oil, sunflower oil, soya bean oil, or castor oil), paraffins, dimethyl sulphoxide, triglycerides and the like. In the case of liquid formulations, the following substances may be used as stabilizers or solubilizers: lower aliphatic mono- and multivalent alcohols with 2-4 carbon atoms such as ethanol, n-propanol, glycerol, polyethylene glycols with molecular weights between 200-600 (e.g., 1 to 40% aqueous solution), gum acacia, guar gum, or other suspension agents selected from the hydrocolloids.

In addition to liquid formulations for oral delivery, solutions or suspensions used for non-oral delivery (e.g., parenteral, intradermal, subcutaneous, or topical) can include any of the following components: a sterile diluent such as water, saline solution, fixed oil, polyethylene glycol, glycerine, propylene glycol, dimethyl acetamide or other synthetic solvents; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the free beta-alanine or a biological source thereof exhibit insufficient solubility, methods for solubilizing free beta-alanine or a biological source thereof may be used. Such methods are known to those of skill in the art and include, but are not limited to, using co-solvents such as dimethylsulfoxide (DMSO), dimethylacetamide, using surfactants such as TWEEN®, or by dissolving the beta-alanine in aqueous sodium bicarbonate.

In one embodiment, beta-alanine or a biological source thereof can be formulated in a liposomal suspension (e.g., tissue-targeted liposomes) for delivery to a human or an animal. A liposomal suspension can be prepared according to methods known to those skilled in the art. See, for example, U.S. Pat. No. 4,522,811. Briefly, liposomes such as multilamellar vesicles (MLV's) may be formed by drying down egg phosphatidyl choline and brain phosphatidyl serine (e.g., at a 7:3 molar ratio) on the inside of a flask. A solution of beta-alanine or a biological source thereof in phosphate buffered saline lacking divalent cations (PBS) is added and the flask shaken until the lipid film is dispersed. The resulting vesicles are washed to remove un-encapsulated beta-alanine, pelleted by centrifugation, and then resuspended in PBS.

Pharmaceutically acceptable carriers are known in the art, and their selection usually is dependent upon the intended route of delivery. Examples of carriers useful in solid and aqueous dispersions according to the compositions and methods provided herein include, but are not limited to, water-soluble polymers such as guar gum, glucommannan, psyllium, gum acacia, polyethylene glycol, polyvinylpyrrolidone, hydroxypropyl methylcellulose, and other cellulose ethers such as methylcellulose, and sodium carboxymethylcellulose. Additional carriers for a liquid composition include, for example, water, saline, aqueous dextrose, glycerol, glycols, ethanol, and the like.

Along with the beta-alanine or a biological source thereof, the composition can contain any number of additional components. For example, a composition containing beta-alanine also can include: a diluent such as lactose, sucrose, dicalcium phosphate, or carboxy methylcellulose; a lubricant, such as magnesium stearate, calcium stearate and talc; and/or a binder such as starch, natural gums, such as gum acaciagelatin, glucose, molasses, polyinylpyrrolidine, celluloses and derivatives thereof, povidone, crospovidones and other such binders known to those of skill in the art. Compositions of the invention further can include disintegrating agents, coloring agents (e.g., any of the approved certified water soluble FD&C dyes), flavoring agents, and wetting agents. Flavoring and sweetening agents are useful, as are preservatives, stabilizers, buffer substances and antioxidants.

The pharmaceutical composition disclosed herein also may contain further substances such as emulsifying agents, solubilizing agents, pH buffering agents, and the like (e.g., acetate, sodium citrate, cyclodextrine derivatives, sorbitan monolaurate, triethanolamine sodium acetate, triethanolamine oleate, and other such agents). Solvents include glycerin, sorbitol, ethyl alcohol and syrup; examples of preservatives include glycerin, methyl and propylparaben, benzoic add, sodium benzoate and alcohol; examples of non aqueous liquids utilized in emulsions include mineral oil and cottonseed oil; examples of emulsifying agents include gelatin, acacia, tragacanth, bentonite, and surfactants such as polyoxyethylene sorbitan monooleate; suspending agents include sodium carboxymethylcellulose, pectin, tragacanth, Veegum and acacia; sweetening agents include sucrose, syrups, glycerin and artificial sweetening agents such as saccharin; and wetting agents include propylene glycol monostearate, sorbitan monooleate, diethylene glycol monolaurate and polyoxyethylene lauryl ether.

Liquid pharmaceutically-administrable compositions can, for example, be prepared by dissolving, dispersing, or otherwise mixing free beta-alanine or a biological source thereof and optional pharmaceutical adjuvants in a carrier, such as, for example, water, saline, aqueous dextrose, glycerol, glycols, ethanol, and the like, to thereby form a solution or suspension. In addition, tablets and capsules formulations may be coated as known by those of skill in the art in order to modify or sustain dissolution of the active ingredient. Thus, for example, they may be coated with a conventional coating such as phenylsalicylate, waxes and cellulose acetate phthalate, or with another enteric coating that maintains its integrity in the stomach and provides sustained release of the beta-alanine. Methods of preparing pharmaceutical compositions are known or will be apparent to those skilled in this art. See, for example, *Remington's Pharmaceutical Sciences*, Mack Publishing Company, Easton, Pa., 15th Edition, 1975.

C. Sustained Release Formulations

The preferred formulation for the compositions containing free beta-alanine or a biological source thereof as described herein is a sustained release formulation. For the purposes of the present invention, the following terms may be considered to be substantially equivalent to 'sustained release': continuous release, controlled release, delayed release, depot, gradual release, long-term release, programmed release, prolonged release, proportionate release, protracted release, repository, retard, slow release, spaced release, time coat, timed release, delayed action, extended action, layered-time action, long-acting, prolonged action, repeated action, slowing acting, sustained action, sustained-action medications, and extended release. Further discussions of these terms may be found in Lesczek Krowczynski, *Extended-Release Dosage Forms*, 1987 (CRC Press, Inc.).

The concentrations of free beta-alanine or a biological source thereof in the compositions disclosed herein are effective for increasing the anaerobic working capacity of a tissue by providing an amount of free beta-alanine to blood or blood plasma effective to increase the synthesis of beta-alanylhistidine peptides, particularly carnosine, in muscle and other tissues. A sustained release formulation of beta-alanine is administered in an amount effective to attenuate the metabolic acidosis encountered during high-intensity exercise and thus delay the onset of fatigue during anaerobic exercise without inducing symptoms of parasthesia.

The concentration of free beta-alanine or a biological source thereof in the pharmaceutical composition will depend on the particular formulation, the rate of absorption, the inactivation and excretion rates of the beta-alanine, the physicochemical characteristics of the beta-alanine, and the dosage schedule as well as other factors known to those of skill in the art. The contemplated compositions, however, may contain 0.001% up to 100% of free beta-alanine or a biological source thereof (e.g., 0.1-85% or 75-95%).

The free beta-alanine or a biological source thereof is included in the pharmaceutically acceptable carrier in an amount sufficient to exert a therapeutically useful effect in the absence of undesirable side effects. The therapeutically effective concentration may be determined empirically by testing an amount of beta-alanine in in vitro and in vivo systems such as those described herein and then extrapolating therefrom for dosages in humans.

Typically, a therapeutically effective dosage should produce a blood, plasma or serum concentration of beta-alanine or an equivalent amount of a biological source thereof to muscle or other tissue of from about 0.1 µg/ml to about 50-100 µg/ml. The pharmaceutical compositions typically should provide a dosage of from about 0.001 mg to about 2000 mg of beta-alanine per kg of body weight per day. Pharmaceutical dosage unit forms are prepared to provide from about 1 mg to about 10,000 mg (e.g., from about 10 to about 5,000 mg) of the beta-alanine per dosage unit form.

The free beta-alanine dosage can be between about 1 milligram (mg) and about 200 mg per kilogram (kg) body weight, or the dose of a biological source thereof (e.g., a peptide of beta-alanine (e.g. carnosine)) can be between about 2.5 mg and about 500 mg per kg body weight. By way of example, suitable controlled release dosages in an 80 kg person per day can be between 0.08 grams to 16.0 grams of free beta-alanine or an equivalent amount of a biological source of beta-alanine. In one aspect, the total amount of free beta-alanine administered in a controlled release dosage per day can be at least 200 mg, from 200 mg to 5 g, from 5 g to 10 g, or from 5 g to 16 g or more per day for a human. A single dose of active ingredient, e.g., free beta-alanine or a biological source thereof, may be formulated to be in the amount about 200, 400, 800, 1600, 3200, 6400 mg or more.

For humans and animals, the compositions disclosed herein can be, for example, (a) 1% to 99% by weight of free beta-alanine or a biological source thereof and 0% to 98% by weight of water; (b) 1% to 98% by weight of free beta-alanine or a biological source thereof and 0% to 97% by weight of water; (c) 1% to 20% by weight of free beta-alanine or a biological source thereof, 9% to 99% by weight of glucose or other simple carbohydrate and 0% to 60% by weight of water; or (d) 1% to 20% by weight of free beta-alanine or 1% to 20% by weight of a peptide of beta-alanine, 9% to 99% by weight of glucose or other simple carbohydrate and 0% to 60% by weight of water.

A particular dosage of beta-alanine can be administered in a single dose or can be divided into a number of smaller doses to be administered at particular intervals of time. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutically therapeutically active free beta-alanine, biological sources of beta-alanine, and derivatives, analogues or conjugates thereof are typically formulated and administered in unit dosage forms or multiple dosage forms. Unit dose forms as used herein refers to physically discrete units suitable for human and animal subjects and packaged individually as is known in the art. Each unit dose contains a predetermined quantity of therapeutically active beta-alanine sufficient to produce the desired therapeutic effect in association with the required pharmaceutical carrier, vehicle or diluent. Unit dose forms may be administered in fractions or multiples thereof. A multiple dose form generally is a plurality of identical unit dosage forms packaged in a single container to be administered in segregated unit dose form. Examples of unit dose forms include ampules and syringes and individually packaged tablets or capsules, and examples of multiple dose forms include vials, bottles of tablets or capsules, and bottles of pints or gallons.

As used herein, sustained release can mean any one of a number of extended release dosage forms. The various sustained release technologies cover a very broad spectrum of drug dosage forms. Sustained release technologies include, but are not limited to, physical systems as well as chemical systems.

Physical systems include, but are not limited to, reservoir systems with rate-controlling membranes such as encapsulation (e.g., micro- and macro-) and membrane systems; reservoir systems without rate-controlling membranes such as hollow fibers, ultra macroporous cellulose triacetate, and porous polymeric substrates and foams; monolithic systems including those systems physically dissolved in non-porous, polymeric, or elastomeric matrices (e.g., non-erodible, erodible, environmental agent ingression, and degradable) and materials physically dispersed in non-porous, polymeric, or elastomeric matrices (e.g., non-erodible, erodible, environmental agent ingression, and degradable); laminated structures including reservoir layers chemically similar or dissimilar to outer control layers; and other physical methods such as osmotic pumps or adsorption onto ion-exchange resins.

Chemical systems include, but are not limited to, chemical erosion of polymer matrices (e.g., heterogeneous or homogeneous erosion) or biological erosion of a polymer matrix (e.g., heterogeneous, or homogeneous). Hydrogels may also be employed as described in "*Controlled Release Systems: Fabrication Technology*", Vol. II, Chapter 3; pages 41-60; "*Gels For Drug Delivery*", Edited By Hsieh, D.

There are a number of sustained release drug formulations that have been developed. These include, but are not limited to, microencapsulated powders; osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gel diffusion controlled gastrointestinal delivery systems; and ion-exchange-controlled gastrointestinal delivery systems, which include cationic and anionic drugs. In one embodiment, the sustained release system can be an oil-microencapsulated sustained release powder dosage form that can be mixed with liquid and consumed as a drink mix beverage. See, also, sustained release formulations developed by Rohm Hass (Philadelphia, Pa.), as well as representative U.S. patents that disclose sustained release formulations (e.g., U.S. Pat. Nos. 6,696,500; 6,756,049; 6,919,372; 6,992,065; and 7,048,947).

Furthermore, many of the conventional pharmaceutical binders, excipients and additives, when used in sufficient quantities, can act as controlled-release polymers and produce a sustained release effect. These include, but are not limited to, gelatin, natural sugars such as raw sugar or lactose, lecithin, mucilage, plant gums, pectins or pectin derivatives, algal polysaccharides, glucomannan, agar and lignin, guar gum, locust bean gum, acacia gum, xanthan gum, carrageenan gum, karaya gum, tragacanth gum, ghatti gum, starches (e.g., corn starch or amylose), dextran, polyvinyl pyrrolidone, polyvinyl acetate, gum arabic, alginic acid, tylose, talcum, lycopodium, silica gel (e.g., colloidal), cellulose and cellulose derivatives (e.g., cellulose ethers, cellulose ethers in which the cellulose hydroxy groups are partially etherified with lower saturated aliphatic alcohols and/or lower saturated, aliphatic oxyalcohols; e.g., methyloxypropyl cellulose, methyl cellulose, hydroxypropyl methyl cellulose, hydroxypropyl methyl cellulose phthalate, cross-linked sodium carboxymethylcellulose, cross-linked hydroxypropylcellulose, high-molecular weight hydroxymethylpropycellulose, carboxymethyl-cellulose, low-molecular weight hydroxypropylmethylcellulose medium-viscosity hydroxypropylmethylcellulose hydroxyethylcellulose, hydroxypropylcellulose, hydroxypropylmethylcellulose, sodium carboxymethylcellulose, alkylcelluloses, ethyl cellulose, cellulose acetate, cellulose propionate (low, medium or high molecular weight), cellulose acetatepropionate, cellulose acetate butyrate, cellulose triacetate, methyl cellulose, hydroxypropyl cellulose, orhydroxypropylmethyl cellulose), fatty acids as well as magnesium, calcium or aluminum salts of fatty acids with 12 to 22 carbon atoms, in particular saturated fatty acids (e.g., stearates such as magnesium stearate), polycarboxylic acids, emulsifiers, oils and fats, in particular vegetable (e.g., peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids (e.g., $C_{12}H_{24}O_2$ to $C_{18}H_{36}O_2$) and their mixtures, it being possible for the glycerol hydroxy groups to be totally or also only partly esterified (e.g., mono-, di- and triglycerides); high melting point hydrogenated vegetable oils suitable for microencapsulation; pharmaceutically acceptable mono- or multivalent alcohols and polyglycols such as polyethylene glycol and derivatives thereof, esters of aliphatic saturated or unsaturated fatty acids (e.g., 2 to 22 carbon atoms, e.g., 10-18 carbon atoms) with monovalent aliphatic alcohols (e.g., 1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_1$-$C_{12}$ alcohols, dimethylacetamide, lactamides, lactates, ethylcarbonates, silicones (e.g., medium-viscous polydimethyl siloxanes), calcium carbonate, sodium carbonate, calcium phosphate, sodium phosphate, magnesium carbonate and the like.

In addition, coating agents may be used to create or enhance the sustained release features of a pharmaceutical composition. For example, plasticizers that are useful as coating agents include, but are not limited to, citric and tartaric acid esters (acetyl-triethyl citrate, acetyl tributyl-, tributyl-, triethyl-citrate); glycerol and glycerol esters (glyceroldiacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths); adipates (diethyladipate, di (2-methoxy- or 2-ethoxyethyl)-adipate; benzophenone; diethyl- and diburylsebacate; dibutylsuccinate; dibutyltartrate; diethylene glycol dipropionate; ethyleneglycol diacetate, -dibutyrate, -dipropionate; tributyl phosphate, tributyrin; polyethylene glycol sorbitan monooleate; polysorbates such as Polysorbar 50; and sorbitan monooleate.

Methods of making sustained release pharmaceutical compositions are known in the art. For example, coating agents such as ethylcellulose and hydroxypropyl methylcellulose can be mixed together and sprayed onto beta-alanine or a biological source thereof in a fluid bed granulator. Another method of making a sustained release pharmaceutical composition employs mixtures of a high temperature melted vegetable oil (e.g., having an iodine value maximum of about 5 and a melting point of about 145° F.) with a cellulose ether such as ethylcellulose. This combination can be processed in a vertical or horizontal high intensity mixer or a blender that is jacketed so as to allow a hot water bath to circulate around the mixer to elevate the temperature of the oil to the melting point. Powdered beta-alanine or a biological source thereof is then mixed with the molten oil until complete coverage is achieved (about 5-10 minutes), cooled, and the ethylcellulose sprayed onto the particles. The finished product is a microencapsulated, free-flowing sustained-release powder with an extended release profile. See, also, U.S. Pat. Nos. 6,835,397; 6,013,286; and 5,190,775 for methods describing controlled release of encapsulated bioactive substances.

In the compositions, effective concentrations of free beta-alanine or a biological source thereof are mixed with a suitable pharmaceutical carrier or vehicle. The free beta-alanine or a biological source thereof may be derivatized as the corresponding salts, esters, enol ethers or esters, acids, bases, solvates, hydrates or pro-drugs prior to formulation, as is known in the art.

D. Dietary Supplements

Dietary supplements formulated for the sustained release of free beta-alanine or a biological source thereof are provided. The dietary supplements may comprise a food product or a liquid product.

1. Solid Food Products

A dietary supplement formulated as a food product can be in a solid or an edible suspension. Solid food products may comprise chewable or edible bars, cookies, biscuits, lozenges, chewing gum, or edible suspension. In one embodiment, the dietary supplement containing free-beta alanine or a biological source thereof is a solid food product in the form of a high-energy multi-saccharide edible bar containing the substance galactose.

In one embodiment, an edible food bar includes a saccharide component including 3 to 37% weight/weight (w/w) galactose, 0.1 to 75% w/w free beta-alanine or a biological source thereof, and optional further ingredients selected from amino acids, carbohydrates, fiber and fat, and other ingredients such as creatine and beta-alanylhistidine peptides (e.g. carnosine, anserine, and/or balenine). The amount of galactose can be, for example, 5 to 20% w/w (e.g., 5 to 15% w/w). The saccharide component also can include glucose. In one embodiment, equal amounts of glucose and galactose are provided. In, another embodiment, the amount of galactose is greater than the amount of glucose.

The invention generally includes the inclusion of free beta-alanine or a biological source thereof with other ingredients to give a bar, drink or other type of food that can be low in glucose and can have a low glycemic index. The use of galactose affords several advantages. For example, galactose is not insulogenic; that is, galactose does not itself induce an insulin response. Thus, its use is associated with less of an insulin response than the equivalent mass of glucose. Products in accordance with this invention may be used by diabetics or persons who are intolerant to lactose. Galactose can be used rapidly by the liver for synthesis of glycogen or glucose, and it is less likely to cause dental erosion than other sugars.

Some embodiments of solid food product compositions containing free beta-alanine incorporate 0.1 to 50% free beta-alanine or a biological source thereof. In order to prevent unwanted adverse side effects, it is desired that the free beta-alanine or a biological source thereof exhibits sustained or delayed release from the food product. For example, the free beta-alanine or a biological source thereof may be contained within a food product and separated from any moist ingredients by, for example, formulation in layers. Alternatively, the free beta-alanine or a biological source thereof may be embodied within the matrix of the food itself, wherein the nature of the matrix delays dissolution of the food within the stomach. Additionally, beta-alanine can be encapsulated as granules or powder in a dry water-impervious shell (e.g., micro-encapsulation) and used in a food product. In this way, the free beta-alanine can be slowly released in the stomach by dissolution.

Use of fiber in a food product (e.g., an energy bar) is advantageous because different fiber products influence the release of sugars, affect the binding of various components and advantageously delay digestion. An amount of between 0 to 5% (or more) w/w sugars may be used in a food product containing beta-alanine or a biological source thereof. Furthermore, a composition containing beta-alanine or a biological source thereof may be absorbed onto the fiber prior to the manufacture of the food product. In this way, the absorption of the beta-alanine into the body may be retarded.

In a layered arrangement, the free beta-alanine powder or aggregate may be covered with a hard dry sugar layer. Alternatively or in addition, a chocolate containing layer may be used as a moisture barrier. A free beta-alanine containing layer may be provided as a laminar cylindrical layer disposed within the bar as the inner layer. Alternatively or in addition, ingredients such as fiber, nuts and dried fruit may be layered onto the layer-containing free beta-alanine to form a laminate. Such a layer may incorporate syrup so as to form a composite-type layer.

In alternative food products, beta-alanine powder or aggregate may be covered with a hard sugar mixture, chocolate or both to form particles with a mass of 100 to 500 mg. These can be combined with the remaining ingredients to form dispersed units within the matrix, for example, as chocolate chips within a cookie. Such an encapsulated arrangement may incorporate layers as previously described.

2. Edible Suspensions

In another embodiment, dietary supplements containing free-beta alanine or a biological source of beta-alanine are food products wherein the free beta-alanine or a biological source of beta-alanine is suspended in an edible supporting matrix to form an edible suspension. The term "suspension" is intended to mean compositions containing free beta-alanine or a biological source of beta-alanine as provided herein, comprise flee beta-alanine in solid form (e.g. as crystals, power or the like), distributed within an edible viscous liquid or semi-liquid, or a solid, supporting matrix, typically such that settling (under the influence of gravity) of the solid beta-alanine is inhibited or prevented.

The composition may be provided in solid, liquid or semi-liquid form (e.g. as a drink, soup or yogurt). Preferably, the free beta-alanine is distributed substantially evenly throughout the supporting matrix (by homogenizing in some manner e.g. by stirring, blending or the like), which may be accomplished manually (e.g. by the consumer) and/or mechanically at the time the composition is prepared.

Conveniently, the food product is an otherwise conventional food product supplemented with free beta-alanine or a biological source of beta-alanine such that beta-alanine becomes suspended in the foodstuff. Examples of foodstuffs that may represent suitable supporting matrices for the composition of the invention include spreadable solids such as dairy or cheese spreads, margarines, meat and fish pastes and spreads and the like. Other convenient supporting matrices are those containing sugars or other carbohydrates, such as liquid ("runny") or solid ("set") honey, molasses, syrup (e.g. corn syrup, glucose syrup), treacle or gels of any description, foods made viscous by cooling including ice-cream, and foods made viscous by cooking and baking, e.g. muffins, pies, tarts, cakes, biscuits and cereal flakes.

If desired, the viscosity of the edible matrix and/or the composition as a whole, may be increased by the addition of viscosifiers, gelling agents and the like. Such components are well-known in the food industry and include, for example, plant-derived polysaccharides, gums and the like such as galactomannans, dextrans, guar gum, locust bean gum and so on. Such viscosifiers, gels and the like may form the supporting matrix, if desired. One representative edible matrix comprises a gel prepared from concentrated *Aloe Vera* extract: a smooth creamy paste, which, for example, can be packaged in a squeezable tube.

The composition may comprise one or more further components to improve its palatability, stability, flavor or nutritive quality. These further components may include electrolytes, vitamins (e.g., vitamin E, vitamin C, thiamin, riboflavin, niacin, vitamin B6, folic acid, vitamin B12, biotin, and pantothenic acid), lipids, carbohydrates (e.g., starch and/or sugars, e.g., glucose, fructose, sucrose, and maltrose), amino acids, trace elements, colorings, flavors, artificial sweeteners, natural health improving substances, anti-oxidants, stabilizers, preservatives, and buffers. The composition may be unflavored or have the normal flavor of the matrix. Alternatively, one or more flavors may be added (e.g. fruit, cheese or fish flavor).

Other ingredients that can be included in the presently disclosed sustained release beta-alanine compositions can include, for example, anti-oxidants, alpha-lipoic acid, tocotrienols, N-acetylcysteine, co-enzyme Q-10, extracts of rosemary such as camosol, botanical anti-oxidants such as green tea polyphenols, grape seed extract, COX-1 type inhibitors such as resveratrol, *ginkgo biloba*, and garlic extracts. Other amino acids such as L-cysteine or L-citrulline may be added. Combination with an acetylcholine precursor such as choline chloride or phosphatidylcholine may be desirable, for example, to enhance vasodilation. It is to be understood that such combination therapy constitutes a further aspect of the compositions and methods of treatment provided herein.

Artificial sweeteners which can be used include Aspartame, Acesulfam K, Saccharin and Cyclamate. Almost any desired flavoring can be added such as fruity flavors such as berry, lemon, orange, papaya and grapefruit. Citric acid may be used as an acidulant and citrate (e.g. sodium citrate) as a buffering agent. Also, other natural health improving substances such as Pan D'Arco tea, Ginseng, Suma tea, Ginkgo, bee pollen and myrrh may be added in physiologically active amounts. Preservatives such as potassium benzoate and/or potassium sorbate can be included. Coloring can be included such as cold water soluble colorant such as beta-carotene. Other suitable colorings, however, will be apparent to those skilled in the art. A clouding agent may be included in the composition, if desired, to improve the appearance of the composition.

Mineral and trace elements also can be added in any type or form which is suitable for human consumption. It is convenient to provide the calcium and potassium in the form of their gluconates, phosphates or hydrogen phosphates, and magnesium as the oxide or carbonate, chromium as chromium picolinate, selenium as sodium selenite or selenate, and zinc as zinc gluconate. Representative amounts include sodium at 400 mg/liter, calcium at 100 mg/liter, chloride at 600 mg/liter, potassium at 200 mg/liter, magnesium at 75 mg/liter and phosphorus at 50 mg/liter, chromium at 125 µg/liter, selenium at 125 µg/liter and zinc at 15 mg/liter.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Example 1

Edible Gel Formulation for the Sustained Release of Free Beta-Alanine

To prepare an edible gel containing free beta-alanine the contents of two packets of commercially available strawberry flavored gelatin gel were dissolved in 200 ml of boiling water.

The contents were stirred continuously until the gel was completely dissolved. The gel was further fortified with the addition of a sachet of gelatin capsules. To this was added 80 g free beta-alanine (in a final volume of approximately 300 ml). The concentrated gel solution was poured into a 12×12 cm flat mould to a depth of approximately 2 cm and allowed to set to a stiff gel at 4° C. One square piece of gel (approximately 2×2×2 cm in size) contained approximately 2 g of beta-alanine.

When the piece of gel containing 2 g beta-alanine was ingested (either as two half pieces), symptoms of paraesthesia were mild in the following 20 minutes, and in some subjects could not be detected at all. In contrast, symptoms of paraesthesia were detected in subjects that ingested 2 g free beta-alanine dissolved in water. Thus the sustained release of free beta-alanine mitigates the symptoms of paraesthesia that are felt when equivalent amounts are administered in a single bolus dose.

Example 2

Dissolution of Beta-Alanine Capsules

Samples. Beta-alanine capsules produced by Balchem Encapsulates (New Hampton, N.Y.; see, for example, U.S. Pat. No. 6,835,397) were filled with lipid coated granules of beta-alanine. Samples were identified as RIA-1743 60%, 70%, 80%, 90% and RIA-1744 60%, 70%, 80%, 90% based on the amount of beta-alanine present.

Experimental Testing. Testing was performed by Natural Alternative Inc.'s Research & Development Laboratory utilizing the Logan Instruments DISSO III, USP test apparatus 3. Dissolution was carried out in 0.1 N hydrochloric acid for the length of six hours. Samples were taken at 1, 2, 3, and 6 hours.

Screens used for the first analysis were single size 40 mesh for the top and bottom caps. The second analysis with RIA-1744 applied two mesh screens for the top and bottom caps: a size 40 mesh screen and a second mesh screen (with slightly larger hole size) were combined. Mesh screens were combined as an effort to contain the granules inside the reciprocating cylinders. Granules were released from the capsules following capsule shell disintegration. Quantitation was performed using HPLC analysis with evaporative light scattering detection.

Results. Tables 1 and 2 show the results using the single mesh screens size 40, and Table 3 shows the analysis of RIA-1744 with double mesh screens. The data show that the 80% and 90% samples of both formulations, RIA-1743 and RIA-1744, demonstrate little sustained release properties. The RIA-1744 60% and 70% formulation demonstrated sustained release properties in both analyses. The 60% formulation had even less beta-alanine dissolved at the end of six hours.

TABLE 1

RIA-1743

| Hour | % Dissolved | | | |
|---|---|---|---|---|
| | 1 | 2 | 3 | 6 |
| 60% | 0.0 | 8.3 | 8.8 | 10.0 |
| 70% | 11.3 | 12.4 | 14.1 | 17.2 |
| 80% | 27.9 | 35.2 | 44.6 | 44.8 |
| 90% | 88.9 | 93.4 | 76.8 | 95.9 |

TABLE 2

RIA-1744

| Hour | % Dissolved | | | |
|---|---|---|---|---|
| | 1 | 2 | 3 | 6 |
| 60% | 18.6 | 33.9 | 49.3 | 74.9 |
| 70% | 26.3 | 46.8 | 62.6 | 81.2 |
| 80% | 88.1 | 90.3 | 73.2 | 91.3 |
| 90% | 96.1 | 94.6 | 93.7 | 93.5 |

TABLE 3

RIA-1744

| Hour | % Dissolved | | | |
|---|---|---|---|---|
| | 1 | 2 | 3 | 6 |
| 60% | 20.8 | 33.1 | 46.4 | 80.4 |
| 70% | 26.2 | 46.7 | 58.0 | 84.8 |
| 80% | 86.4 | 94.4 | 92.5 | 98.1 |

Example 3

Sustained Release Formulation Compared to a Non-Sustained Release Formulation

Two subjects were given 1.75 g beta-alanine dissolved in water (formulated as a drink) or 5 capsules, each containing 0.35 g beta-alanine in a delayed release formulation. Subjects reported symptoms of paraesthesia affecting the face, scalp, neck, arms, hands and buttocks with 1.75 g of beta-alanine administered in a drink, but not with 1.75 g administered in the delayed release capsule formulation. Results (mean±SE) are shown in FIG. 1.

Example 4

Sustained Release Formulations

Subjects were given capsules containing 400 mg beta-alanine but as formulations composed of 100%, 90%, 80%, 70% and 60% beta-alanine, with the balance comprising a lipid mixture to delay dissolution. Two different lipid mixtures were used, referred to herein as mixtures "A" and "B".

Figure 2:
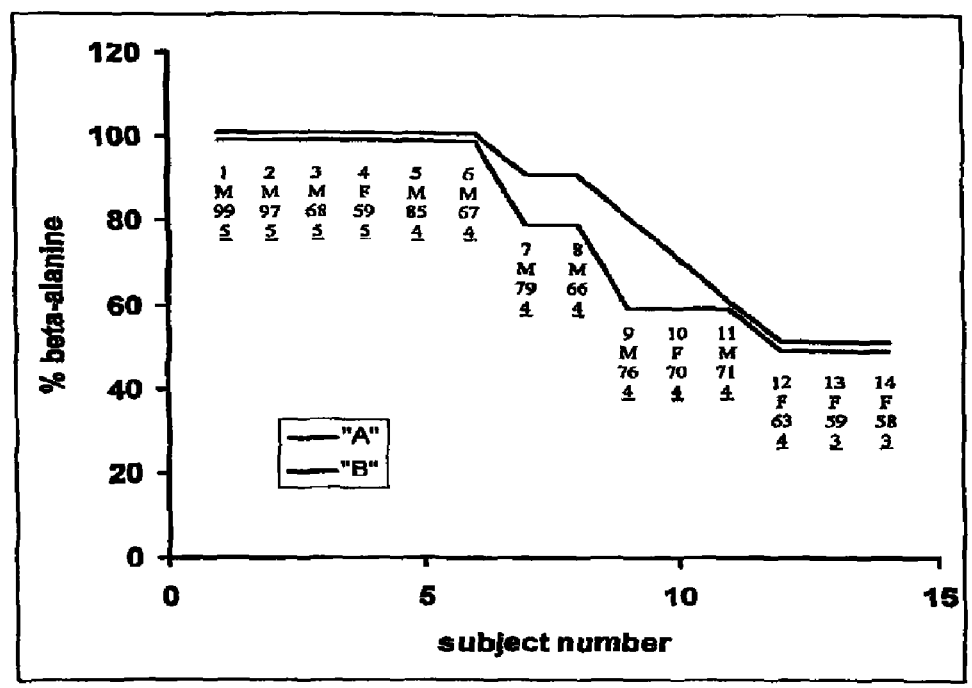
FIG. 2 is a graph showing the blood plasma levels of beta-alanine in individuals following ingestion of two different sustained release beta-alanine formulations.

FIG. 2 shows the compositions of "A" and "B" that contained the highest beta-alanine concentration in which paraesthesia symptoms were not recorded. Each column of figures denotes (from top to bottom): subject number; gender; weight (kg); and number of 400 mg capsules ingested.

Subjects 1-6 did not record paraesthesia symptoms even when the capsules were entirely (i.e., 100%) beta-alanine. Subjects 1-4 took 5 capsules at each dose and subjects 5-6 took 4 capsules at each dose. Subjects 7-10 went to a lower % of beta-alanine before paraesthesia symptoms disappeared completely, more so when taking mixture "B" compared to mixture "A". Each of subjects 7-10 took 4 capsules at each dose. Subjects 11-14 were more sensitive to the paraesthesia effects of beta-alanine that the other subjects, recording the highest grade symptoms at 100% beta-alanine. No paraesthesia symptoms were experienced by subject 11 with 60% beta-alanine in either mixture "A" or "B". Subjects 12-13 still experienced mild paraesthesia symptoms at 60% beta-alanine in either mixture and were, therefore, projected as being symptom free at 50% in either mixture. Subjects 13 and 14 took just 3 capsules at each dose.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing accumulation of beta-alanylhistidine peptide in muscle tissue to delay onset of muscle fatigue in a subject while decreasing the effects of paraesthesia, the method comprising the step of:
administering free beta-alanine, an ester or a salt thereof, to the subject over time in an amount effective to cause accumulation of beta-alanylhistidine peptide in the muscle tissue of the subject,
wherein the free beta-alanine, the ester or the salt thereof, is in a sustained release formulation that decreases the effects of paraesthesia in the subject,
wherein the free beta-alanine, ester or salt thereof, in the sustained release formulation is provided in an amount ranging from about 0.1 to about 10.0 grams, and
wherein the sustained release formulation is provided in a daily dose effective to increase levels of beta-alanine in the subject's blood or blood plasma.

2. The method of claim 1, wherein the free beta-alanine, ester or salt thereof, in the sustained release formulation is provided in an amount ranging from about 1.0 to about 10.0 grams.

3. The method of claim 1, wherein the free beta-alanine, ester or salt thereof, in the sustained release formulation is provided in an amount ranging from about 1.0 to about 9.0 grams.

4. The method of claim 1, wherein the free beta-alanine, ester or salt thereof, in the sustained release formulation is provided in an amount ranging from about 2.0 to about 8.0 grams.

5. The method of claim 1, wherein the free beta-alanine, ester or salt thereof, in the sustained release formulation is provided in an amount ranging from about 3.0 to about 7.0 grams.

6. The method of claim 1, wherein the free beta-alanine, ester or salt thereof, in the sustained release formulation is provided in an amount ranging from about 4.0 to about 6.0 grams.

7. The method of claim 1, wherein the sustained release formulation is in a solid, liquid or semi-liquid.

8. The method of claim 1, wherein the sustained release formulation is part of a drink, energy bar, edible suspension or food stuff.

9. The method of claim 7, wherein components in the sustained release formulation retard absorption of beta-alanine into the body.

10. The method of claim 7, wherein part of the free beta-alanine is found in an emulsion.

* * * * *